United States Patent
Frielinghaus et al.

(10) Patent No.: US 12,133,693 B2
(45) Date of Patent: Nov. 5, 2024

(54) METHOD FOR AUTOMATIC DETECTION OF INSTRUMENT ORIENTATION FOR ROBOTIC SURGERY

(71) Applicant: Brainlab AG, Munich (DE)

(72) Inventors: Nils Frielinghaus, Munich (DE); Mohamed Ahmed Fouad Barakat, Munich (DE)

(73) Assignee: Brainlab AG, Munich (DE)

( * ) Notice: Subject to any disclaimer, the term of this patent is extended or adjusted under 35 U.S.C. 154(b) by 263 days.

(21) Appl. No.: 16/646,786

(22) PCT Filed: Jul. 17, 2019

(86) PCT No.: PCT/EP2019/069270
§ 371 (c)(1),
(2) Date: Mar. 12, 2020

(87) PCT Pub. No.: WO2020/016312
PCT Pub. Date: Jan. 23, 2020

(65) Prior Publication Data
US 2020/0261161 A1    Aug. 20, 2020

(30) Foreign Application Priority Data

Jul. 20, 2018    (WO) .................. PCT/EP2018/069791

(51) Int. Cl.
*A61B 34/20* (2016.01)
*A61B 34/30* (2016.01)
(Continued)

(52) U.S. Cl.
CPC .............. *A61B 34/20* (2016.02); *A61B 34/30* (2016.02); *A61B 2034/2055* (2016.02);
(Continued)

(58) Field of Classification Search
CPC .. A61B 2017/00725; A61B 2034/2055; A61B 2034/2059; A61B 2090/3945;
(Continued)

(56) References Cited

U.S. PATENT DOCUMENTS

2006/0142657 A1    6/2006  Quaid et al.
2007/0015997 A1*   1/2007  Higgins .................. A61B 5/06
                                                    600/407
(Continued)

FOREIGN PATENT DOCUMENTS

EP        3295339 A1    3/2018
WO    2013/0189520 A1   12/2013
(Continued)

OTHER PUBLICATIONS

International Search Report and Written Opinion for corresponding International Application No. PCT/EP2019/069270, dated Oct. 9, 2019. 14 Pages.

(Continued)

*Primary Examiner* — Scott Luan
(74) *Attorney, Agent, or Firm* — Tucker Ellis LLP

(57) ABSTRACT

A method for automatic detection of a medical instrument orientation for robotic surgery is presented. The method determines the orientation of a marker device attached to the medical instrument in relation to the robotic system by comparing movement information. The method compares the information about a movement of the marker device from a tracking system with the information about a movement of the robotic arm, which movement data can be acquired by the robotic system. The orientation of the medical instrument with respect to the robotic system can be determined automatically and used for subsequent calculations such as an automatic and efficient precise alignment to a target trajectory or a correct positioning assistance for a (Continued)

mechatronic arm. A computer-implemented medical method of automatically determining an orientation of a medical instrument base in relation to a robotic system is provided.

20 Claims, 6 Drawing Sheets

(51) Int. Cl.
*A61B 90/00* (2016.01)
*A61B 90/50* (2016.01)

(52) U.S. Cl.
CPC .......... *A61B 2034/2059* (2016.02); *A61B 2090/3945* (2016.02); *A61B 2090/3983* (2016.02); *A61B 90/50* (2016.02)

(58) Field of Classification Search
CPC . A61B 2090/3983; A61B 34/20; A61B 34/30; A61B 90/50
See application file for complete search history.

(56) References Cited

U.S. PATENT DOCUMENTS

| 2014/0275955 | A1 | 9/2014 | Crawford et al. |
| 2017/0084027 | A1 | 3/2017 | Mintz et al. |
| 2017/0265774 | A1* | 9/2017 | Johnson ................ A61B 5/064 |

FOREIGN PATENT DOCUMENTS

| WO | 2016114834 A2 | 7/2016 |
| WO | 2018024322 A1 | 2/2018 |
| WO | 2018081136 A2 | 5/2018 |

OTHER PUBLICATIONS

International Preliminary Report on Patentability for corresponding International Application No. PCT/EP2019/069270, dated Feb. 4, 2021. 11 pages.
Lars Eirik Bø et al., "Versatile robotic probe calibration for position tracking in ultrasound imaging" 2015 Phys. Med. Biol. 60 3499, Apr. 9, 2015. 16 Pages.
Office Action in IL Application No. 273264, mailing date Apr. 30, 2024, 3 pages.

* cited by examiner

METHOD FOR AUTOMATIC DETECTION OF INSTRUMENT ORIENTATION FOR ROBOTIC SURGERY

RELATED APPLICATION DATA

This application is a national phase application of International Application No. PCT/EP2019/069270 filed Jul. 17, 2019, which claims priority to International Application No. PCT/EP2018/069791, filed on Jul. 20, 2018, the contents of each of which are incorporated herein by reference.

FIELD OF THE INVENTION

The present invention relates to the field of robotic surgery. In particular, the present invention relates to a computer-implemented medical method of automatically determining an orientation of a medical instrument base in relation to a robotic surgery system, a corresponding computer program, a non-transitory program storage medium storing such a program, as well as robot control system and a navigation system for computer-assisted surgery.

TECHNICAL BACKGROUND

Robotic surgery has become increasingly popular amongst medical practitioners over the last years. Robotic surgery systems generally comprise mechatronic arms, semi-robotic systems and fully robotic systems. Such robotic surgery systems may make use of an external tracking system, like for example an optical tracking system, for tracking surgical instruments attached to it. In this case, the orientation of the instrument and thereby the marker device or tracker often needs to be adjustable relative to the robotic arm by providing one or more rotational degrees of freedom so that it is e.g. visible to the optical tracking system.

The inventors of the present invention have found out that this creates a challenge in that the orientation of the adjustable marker device in relation to the robotic system is not clearly defined whereas the information about this position may be required in order to efficiently control the movement of the robotic system to a surgery target, e.g. a trajectory that is specified in the tracking system's coordinate space.

This problem has been addressed in the prior art so far in that either no additional tracking system is used. Alternatively, in the prior art the tracker is firmly attached to the robot and cannot be individually oriented, or the instrument is only mounted in a single fixed orientation. In some other known approaches, the instrument is mounted in one of a set of fixed orientations and the user manually selects the appropriate mounting orientation.

It must be noted that the present invention can be used for any kind of robotic surgery systems comprising mechatronic arms, semi-robotic systems and fully robotic systems, such as e.g. the Cirq™, which is a product of Brainlab and a universal platform for robotic tasks, serving a range of neurosurgical indications.

Aspects of the present invention, embodiments, examples and exemplary steps are disclosed in the following. Different embodiments, examples and exemplary features of the invention can be combined in accordance with the invention wherever technically expedient and feasible.

EXEMPLARY SHORT DESCRIPTION OF THE INVENTION

In the light of the prior art described hereinbefore, it may be seen as the object of the present invention to facilitate an improved control of the movement of robotic surgery systems.

In the following, a short description of the specific features of the present invention is given which shall not be understood to limit the invention only to the features or a combination of the features described in this section.

A method for automatic detection of a medical instrument orientation for robotic surgery is presented.

In particular, this method determines the orientation of a marker device attached to the medical instrument in relation to the robotic system by comparing movement information. In detail, it compares the information about a movement of the marker device from a tracking system with the information about a movement of the robotic system, e.g. of one robotic arm, which movement data are acquired by the robotic system. One technical effect of the invention is that the orientation of the medical instrument with respect to the robotic system can be determined automatically and used for subsequent calculations such as e.g. an automatic and efficient precise alignment to a target trajectory or a correct positioning assistance for e.g. said mechatronic arm. Therefore, a computer-implemented medical method of automatically determining an orientation of a medical base in relation to a robotic system is provided, as will be explained in more detail hereinafter.

For this purpose both a tracking system as well as movement data about the movement of the robotic system from e.g. position sensors or the motor control of the robotic system can be used. Also other means may be used to acquire the movement data of the robotic system.

As was indicated hereinbefore, movement data provided by the robotic system itself is used in combination with an additional tracking system, e.g. an optical tracking system for tracking surgical instruments attached to the robotic system. In the robotic system, for which this computer-implemented medical method can be applied, the marker device is attached to the medical instrument and the medical instrument is movably attached to the robotic system. Thus, the medical instrument can be moved—while the elements of the robotic system remain fixed—to a desired position and/or desired orientation. Depending on the degrees of freedom in which the medical instrument can be oriented relative to the robotic system, one can constrain the calculation of the presented method to these dimensions. This may save computational effort and may accelerate carrying out the computer-implemented medical method.

As will become apparent from the embodiments elucidated in detail hereinafter, for said medical instrument the more generic terminology "medical instrument base" is used, since it may be realized as e.g. a guiding tube configured for receiving a surgical instrument or may be realized e.g. as an instrument shaft of a surgical instrument.

GENERAL DESCRIPTION OF THE INVENTION

In the following section, a description of the general features of the present invention is given, for example by referring to possible embodiments of the invention.

As stated above, it may be desirable to facilitate for an improved control of the movement of robotic surgery systems.

This is achieved by the subject-matter of the independent claims, wherein further embodiments are incorporated in the dependent claims and the following description.

The described embodiments similarly pertain to the method of automatically determining an orientation of a medical instrument base in relation to a robotic system, the computer program, the program storage medium, the robot control system and the navigation system for computer-assisted surgery. Synergetic effects may arise from different combinations of the embodiments although they might not be described in detail hereinafter. Furthermore, it shall be noted that all embodiments of the present invention concerning a method, might be carried out with the order of the steps as explicitly described herein. Nevertheless, this has not to be the only and essential order of the steps of the method. The herein presented methods can be carried out with another order of the disclosed steps without departing from the respective method embodiment, unless explicitly mentioned to the contrary hereinafter.

Technical terms are used by their common sense. If a specific meaning is conveyed to certain terms, definitions of terms will be given in the following in the context of which the terms are used.

According to a first aspect of the present invention, a computer-implemented medical method of automatically determining an orientation of a medical instrument base in relation to a robotic system is presented. The method comprises the step of acquiring first movement data associated with a movement of the robotic system relative to a first reference. Furthermore, acquiring second movement data associated with a movement of a marker device relative to a second reference is comprised by the method. The marker device is attached to the medical instrument base and the medical instrument base is movably attached to the robotic system. The method further comprises the steps of comparing the first and second movement data and determining a comparison result. Said comparison result is used for determining the orientation of the medical instrument base in relation to the robotic system.

In other words, the method presented herein is directed to the determination of the orientation of the marker device in relation to the robotic system by comparing the information about a movement of both the marker device as well as of the robotic system. Therefore, in contrast to prior art approaches, in this aspect of the present invention, an additional tracking system can be used, the marker device is movably attached to the robot and can be oriented individually—via the movable attachment of the medical instrument base to the robotic system. Further, the medical instrument can be mounted in several fixed orientations and the user does not have to select appropriate mounting orientations manually.

Speaking generally, since the marker device is attached to the medical instrument base preferably in a fixed manner, tracking the marker device results in tracking the medical instrument base. In other words, since the marker device cannot move relative to the medical instrument base due its fixation, it is possible to gather the second movement data of the medical instrument base by tracking the tracking device. The movement of the marker device detected during tracking thus correlates or equals to the movement of the medical instrument base.

It is to be noted that different kinds of marker devices, tracking systems and procedures may be used to track the movement of the marker device. This will be described in more detail hereinafter. Moreover, various different kinds of medical instrument bases can be used like for example a guiding tube or a shaft of a surgical instrument. Also this will be explained in more detail hereinafter.

The method of the present invention thus provides a clearly defined orientation of the marker device in relation to the robotic system. This information can be beneficially used in order to efficiently control movements of the robotic system to for example a surgery target. The determined orientation of the medical instrument base in relation to the robotic system may for example be used to align the medical instrument base with a trajectory that is specified and to be used for surgery purposes.

It should again be noted that the method of the present invention is applicable to any kind of robotic surgery systems, in particular to mechatronic arms, semi-robotic systems and fully robotic systems. Further, in general, the medical instrument base can be connected to the robotic arm via different kind of joints, like a cylindrical receiving section or a ball joint, as will be described in detail hereinafter.

In contrast to prior art solutions, the user of the present invention does not have to trust the position sensors of the robotic systems. Moreover, with the present invention the usability of the marker device is not impaired by not having the flexibility to adequately orient it. Thus, line of sight issues such that the marker device can no longer be detected or only be detected with reduced accuracy are avoided by the present invention. Moreover, in contrast to some prior art approaches, the present invention does not require additional manual steps. In general, the present invention may increase the precision of robot assisted surgery.

Since the marker device is attached to the medical instrument base, and since the medical instrument base is movably attached to the robotic system, also the marker device is provided in a movable manner relative to the robotic system. This will be explained in more detail with respect to embodiment examples and in particular with respect to the examples shown in FIGS. 2 and 3. The present invention thus allows for adjusting the orientation of the medical instrument via the medical instrument base being movable relative to the robotic system by one or more degrees of freedom. Hence, the marker device can be adjusted into a visible position such that it is visible for the tracking system used in combination with the present invention. The result of the presented method, i.e. the determined orientation, can be used by a robot control system for controlling the robot arm before, during, or after surgery and may also be used by a navigation system for computer assisted surgery.

According to another exemplary embodiment, the method is a calibration method for the robotic system. In a further preferred embodiment, the method is not carried out during surgery.

It should also be noted that the first and second movements may occur/are caused simultaneously or sequentially.

In the following definitions for the terms used in in the context of the first aspect of the present invention are provided.

Computer-Implemented Method

The method in accordance with the invention is for example a computer-implemented method. For example, all the steps or merely some of the steps (i.e. less than the total number of steps) of the method in accordance with the invention can be executed by a computer (for example, at least one computer). An embodiment of the computer-implemented method is a use of the computer for performing a data processing method. An embodiment of the computer-implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating or determining steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is a virtual reality device or an augmented reality device (also referred to as virtual reality glasses or augmented reality glasses) which can be used as "goggles" for navigating. A specific example of such augmented reality glasses is Google Glass (a trademark of Google, Inc.). An augmented reality device or a virtual reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. An example of such a digital lightbox is Buzz®, a product of Brainlab AG. The monitor may also be the monitor of a portable, for example handheld, device such as a smart phone or personal digital assistant or digital media player.

Acquiring Data

The expression "acquiring data" for example encompasses (within the framework of a computer-implemented method) the scenario in which the data are determined by the computer-implemented method or program. Determining data for example encompasses measuring physical quantities and transforming the measured values into data, for example digital data, and/or computing (and e.g. outputting) the data by means of a computer and for example within the framework of the method in accordance with the invention. The meaning of "acquiring data" also for example encompasses the scenario in which the data are received or retrieved by (e.g. input to) the computer-implemented method or program, for example from another program, a previous method step or a data storage medium, for example for further processing by the computer-implemented method or program. Generation of the data to be acquired may but need not be part of the method in accordance with the invention. The expression "acquiring data" can therefore also for example mean waiting to receive data and/or receiving the data. The received data can for example be inputted via an interface. The expression "acquiring data" can also mean that the computer-implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured for example by a tracking device or at least one position sensor of the robotic system. Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired.

Marker Device

A marker device can for example be a reference star or a pointer or a single marker or a plurality of (individual)

markers which are then preferably in a predetermined spatial relationship. The latter is referred to as marker array herein. A marker device comprises one, two, three or more markers, as exemplarily shown in FIGS. 2, 3, and 4 wherein two or more such markers are in a predetermined spatial relationship. This predetermined spatial relationship is for example known to a navigation system and is for example stored in a computer of the navigation system.

In another embodiment, a marker device comprises an optical pattern, for example on a two-dimensional surface. The optical pattern might comprise a plurality of geometric shapes like circles, rectangles and/or triangles. The optical pattern can be identified in an image captured by a camera, and the position of the marker device relative to the camera can be determined from the size of the pattern in the image, the orientation of the pattern in the image and the distortion of the pattern in the image. This allows determining the relative position in up to three rotational dimensions and up to three translational dimensions from a single two-dimensional image.

The position of a marker device can be ascertained, for example by a navigation system. If the marker device is attached to an object, such as a bone or a medical instrument, the position of the object can be determined from the position of the marker device and the relative position between the marker device and the object. Determining this relative position is also referred to as registering the marker device and the object. The marker device or the object can be tracked, which means that the position of the marker device or the object is ascertained twice or more over time.

Marker

It is the function of a marker to be detected by a marker detection device (for example, a camera or analytical devices such as CT or MRI devices) in such a way that its spatial position (i.e. its spatial location and/or alignment) can be ascertained. The detection device is for example part of a navigation system. The markers can be active markers. An active marker can for example emit electromagnetic radiation and/or waves which can be in the infrared, visible and/or ultraviolet spectral range. A marker can also however be passive, i.e. can for example reflect electromagnetic radiation in the infrared, visible and/or ultraviolet spectral range or can block x-ray radiation. To this end, the marker can be provided with a surface which has corresponding reflective properties or can be made of metal in order to block the x-ray radiation. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can however also exhibit a cornered, for example cubic, shape.

Reference Star

A "reference star" refers to a device with a number of markers, advantageously three markers, attached to it, wherein the markers are (for example detachably) attached to the reference star such that they are stationary, thus providing a known (and advantageously fixed) position of the markers relative to each other. The position of the markers relative to each other can be individually different for each reference star used within the framework of a surgical navigation method, in order to enable a surgical navigation system to identify the corresponding reference star on the basis of the position of its markers relative to each other. It is therefore also then possible for the objects (for example, instruments and/or parts of a body) to which the reference star is attached to be identified and/or differentiated accordingly. In a surgical navigation method, the reference star serves to attach a plurality of markers to an object (for example, a bone or a medical instrument) in order to be able to detect the position of the object (i.e. its spatial location and/or alignment). Such a reference star for example features a way of being attached to the object (for example, a clamp and/or a thread) and/or a holding element which ensures a distance between the markers and the object (for example in order to assist the visibility of the markers to a marker detection device) and/or marker holders which are mechanically connected to the holding element and which the markers can be attached to.

In the following preferred embodiments will be described in more detail.

According to another exemplary embodiment of the present invention, the acquisition of the first movement data associated with the movement of the robotic system is not based on tracking a marker positioned at a housing of the robotic system.

In other words, the acquisition of the first movement data is carried out marker-less. As is understood and appreciated by the skilled reader, this description of the marker-less data acquisition of the first movement data on the robot side, i.e. not on the medical instrument side, still entails the use of the marker mentioned hereinbefore for acquiring the second movement data, which relate to the movement of the medical instrument base. Thus, this embodiment of the invention is an advantageous combination of marker-less and marker-based data acquisition, as will be elucidated in more detail hereinafter.

As is understood by the skilled reader and as will be explained hereinafter in more detail, this marker-less based data acquisition about the robot movement may entail further steps like transferring the first and second movement data into the same coordinate system using an assumed relationship, preferably a default orientation, and comparing the determined orientation with the assumed relationship thereby deducing the actual orientation. Moreover, determining a relative movement of the robotic system from the first movement data of the robotic system and determining a relative movement of the medical instrument base from the second movement data may be comprised. Said relative movements may then be compared to determine the desired orientation of medical instrument base relative to the robotic system. This will be explained in more detail in the context of exemplary embodiments.

According to another exemplary embodiment, the method comprises the step of moving the robotic system for the purpose of determining the orientation of the medical instrument base in relation to the robotic system.

In other words, in this presented embodiment the robotic system is caused to move during a calibration phase in which said orientation is determined before the robotic system is actually applied.

According to another exemplary embodiment of the present invention, the first movement data are acquired from an encoder of the robotic system as encoder data.

Preferably, in this embodiment the second movement data are acquired from an additional, e.g. an optical, tracking system for tracking the medical instrument base by means of the marker device which is attached to the medical instrument base. Thus, also in this embodiment the acquisition of the movement data of the robotic system is not based on tracking a marker positioned at a housing of the robotic system and hence this is done marker-less, whereas the acquisition of the movement data of the medical instrument base relies on the use of a marker as mentioned herein before. This unknown combination of data acquisitions in the field of medical robots and the corresponding subsequent data processing for the determination the orientation of the medical instrument base in relation to the robotic system has the technical advantage that no additional marker is needed on the outside of the housing of the robot. The inventors of the present invention have identified that such an additional marker can severely harm the medical workflow of the practitioner. Hence, this embodiment provides a more natural workflow for the medical practitioner and avoids any out of sight problem of the additional marker that is essentially needed in prior art methods.

According to another exemplary embodiment of the present invention, the encoder data are measured in a first coordinate system, and the second movement data associated with the movement of the marker device are measured in a second coordinate system, which is different from the first coordinate system.

According to another exemplary embodiment of the present invention, the robotic system is actuator-less.

In other words, in this embodiment the robotic system is a passive robotic system, which is moved manually by the operator into the desired position. Therefore, the robotic system cannot cause a movement of some of its parts on its own, but move only in space as a reaction of an external force applied to the robotic system. Thus, no actuators are comprised within the robotic system and hence no actuator data can be used.

According to another exemplary embodiment, the robotic system is an active robot comprising actuators. According to another exemplary embodiment, the robotic system is an active robot comprising actuators, but the robot is moved during the method of determining the orientation of the medical instrument base in relation to the robotic system manually by the operator of the robot.

According to another exemplary embodiment of the present invention, the first reference is a base of the robotic system. Furthermore, the marker device is embodied as a first marker array used in combination with an optical tracking system. Furthermore, the second reference is either a second marker array or a reference of the optical tracking system.

Thus, in this embodiment the first movement data about the robotic system from an initial to a final position relative to the base of the robotic system can be acquired. Further, the optical tracking system acquires the second movement data about the medical instrument base, i.e. the movement of the first marker array that is tracked from an initial to a final position relative to the second marker array or the reference of the optical tracking system is acquired. Again, since the marker device cannot move relative to the medical instrument base due a fixation at the base, it is possible to gather the second movement data of the medical instrument base by tracking the tracking device.

According to another exemplary embodiment of the present invention, the method comprises the step of using the determined orientation of the medical instrument base in relation to the robotic system for controlling the robotic system to align the medical instrument base to a target trajectory, or to provide positioning assistance for a mechatronic arm of the robotic system.

This embodiment describes an exemplary purpose and use of the outcome of the determination of the orientation as described hereinbefore. It should be noted that the robot control system of the present invention and the navigation system for computer-assisted surgery, as will be described hereinafter in more detail, can preferably be configured to carry out this method and be configured to generate corresponding control signals to control e.g. the robot arm to move to a desired position and/or orientation of the medical instrument base.

This embodiment of the present invention comprises different examples with respect to the alignment of the medical instrument base. In particular, said alignment may be carried out automatically, semi-automatically or also manually. In the automatic alignment embodiment, a signal may be generated by the robot control system in order to move the robotic system into a desired position. In the semi-automatic embodiment, the user may first coarsely move the robotic system to a first position and the robot control system may further generate a signal to subsequently move the robotic system from the first position to its final, desired position; this may also be carried out vice versa. In the manual embodiment, the robot control system may generate a signal to the user, for example a graphical signal to be shown to the user on a display of the robotic system, such that the user may purely manually move the robotic system towards a desired position indicated by said signal of the robot control system.

According to another exemplary embodiment of the present invention, the step of acquiring first movement data comprises recording at least an initial position and a final position of the robotic system. Furthermore, the step of acquiring second movement data comprises recording at least an initial position and a final position of the marker device. In this embodiment, the method further comprises determining a relative movement of the robotic system from its initial to its final position and comprises determining a relative movement of the medical instrument base from its initial to its final position. Moreover, the step of comparing the first and second movement data comprises comparing the relative movement of the robotic system with the relative movement of the medical instrument base.

The result of this relative movement comparison can then be used for determining the orientation of the medical instrument base in relation to the robotic system as has been explained before and as is shown in for example in FIG. 1 with step S4.

In this embodiment, the orientation of the medical instrument base can be calculated by for example defining two time points, based on positional change activity, that are considered as the start and the end point of the movement and looking at the relative movement from the start to the end point. For example, one may have a look at the relative movement from the start to the end time point of the interface point of the medical instrument base based on the information received from the additional, external tracking system and of the tool center point (TCP) of the robotic system based on the information from e.g. position sensors of the robotic system.

In an embodiment, these two relative movements can be expressed by an affine transformation in 3D space I and R, where I denotes the relative movement of the medical instrument base relative to its mount and R denotes the relative movement of the robotic system at the instrument mount base. The transformation $R*I^{-1}$ is representative of the orientation of the medical instrument base at the TCP.

In general, a "reference" as described herein, is used for measuring the respective movement. However, the movement of the medical instrument base itself can then be described relative to e.g. the mount of the medical instrument base. The same holds true for the movement of the robotic system, which can then be described relative to e.g. the instrument mount base. The references are only needed to measure the relative movement which can then be expressed with respect to the medical instrument base mounting point or its receiving section—this is why the references can be chosen arbitrarily as long as they are guaranteed to be stable while moving. Thus, in an embodiment of the present invention the movement of the medical instrument base is described relative to the mount of the medical instrument base and the movement of the robotic system is described relative to the instrument mount base. This embodiment can be combined with any other embodiment as described herein.

Further, the term "tool center point" (TCP) is a term commonly used in robotics to describe the point at the distal end of the robot that is usually supposed to be controlled. In a preferred example, this would be a defined center of the receiving section of the robotic system that holds the medical instrument base. Such a receiving section may be formed cylindrically in one embodiment, as is described in the context of the embodiment of FIG. 2. Control movements of robotic systems are often specified in the tool center point coordinate system, since this is convenient for the user. This embodiment also comprises the conversion into position sensor values for individual joints by applying the inverse kinematics calculation which in complex cases can be done for example by numerical optimization methods like e.g. the "Jacobian Pseudo-Inverse" method, which is known to the person skilled in the art.

Furthermore, regarding the affine transformations of this exemplary embodiment, the following background information should be noted. The relative spatial position of an entity in a reference coordinate system can be described by a translation and a rotation of the entity. This represents an affine transformation from the reference to the entity coordinate system (or inverse) in the mathematical sense and is frequently expressed by a 3×4 or 4×4 matrix whereby the determinant of the matrix needs to be 1, because otherwise this would express scaling or mirroring or shearing etc. In the context of the present invention, one may be interested in the position of the medical instrument base with respect to the reference marker and the position of the TCP with respect to the robot base (calculated from the position sensors and the "forward kinematics"). Given the information for a start and an end position of a movement, one can determine the relative movement in the medical instrument base coordinate system and TCP coordinate system—respectively—by applying the inverse transformation of the start position first (going from the instrument or TCP coordinate system to the reference) and then the transformation for the end position (going back from the reference to the updated instrument or TCP coordinate systems). In case that those two coordinate systems have a common origin, the orientation is then defined by the inverse relative movement of the TCP times the relative movement of the medical instrument base. In case that these coordinate systems do not have a common origin, an additional transformation needs to be considered that adjusts those coordinate systems to another.

According to another exemplary embodiment of the present invention, the medical instrument base is movable relative to the robotic system in n degrees of freedom. The method further comprises the step of setting constraints for the step of determining the orientation of the medical instrument base, wherein said constraints are associated with said n degrees of freedom.

This embodiment relates to robotic systems in which the medical instrument base can be oriented relative to the robotic system in n degrees of freedom only. Thus, a mechanical and/or electrical constraint reduces the movability of the medical instrument base.

Generally, the most common scenarios would be to have n=1, 2 or 3 rotational degrees of freedom (DOF). In this case, one can e.g. omit the translational component of the relative movement matrix and determine the (3) Euler angles of the rotational component of the matrix with regards to the main axis of the rotational DOF's and omit 3-n of them. Another approach is to use one or multiple sample points that are not fix points of the relative movement, apply the transformation to them and determine the required parameters from the comparison of the transformed and the original position.

For example, if the medical instrument base can only be rotated around its center axis, one only needs to inspect the difference in the rotation around this axis during the method as described hereinbefore. More details about this embodiment can be gathered from FIG. 2. In such an embodiment, the calculation of the method of the present invention can be constraint to this single dimension. This may reduce the calculation time and/or power needed for carrying out the computer-implemented method. Thus, computational effort is saved and carrying out the computer-implemented medical method may be accelerate.

As has been explained hereinbefore, the robotic system may have a receiving section that receives and holds the medical instrument base during operation of the robotic system. For example, such a receiving section may be cylindrically shape to receive a medical instrument base in form of a shaft that can then be rotated around the centre axis of the receiving section. This can be gathered from e.g. FIG. 2 and the corresponding description herein. It should be noted that different adapters of the robotic system may be used, which provide said receiving section. Moreover, such adapters may have different angles between the centre axis of the receiving section and the robotic system. For such a situation, the present invention provides a further exemplary embodiment, which is of particular advantage. According to this exemplary embodiment of the invention, the computer-implemented medical method of automatically determining the orientation of the medical instrument base also comprises the step of determining the angle between the centre axis of the receiving section and the robotic system. A particular reference of the robotic system, like e.g. a main axis of the robotic system, may be used to describe the angle between the centre axis of the receiving section and the robotic system. Thus, with this embodiment it is determined via the angle determination carried out by the computer-implemented method what kind of adapter is used in the individual case. As is described in the context of the exemplary embodiment of FIG. 2 hereinafter, the instrument shaft 303, to which the marker array 304 is attached, is rotatable along the center axis and can thus rotate around the cylindrical receiving section 306 of the robotic system 300 in which the shaft is received. Therefore, the method of the present invention described herein can comprise the step of determining said angle between the centre axis around which the medical instrument inserted into said base can be rotated and between the robotic system thereby identifying the kind of adapter used in the individual case. The terminology "kind of adapter" shall be understood in a way that the kind specifies which angle between the centre axis of rotation and the robotic system is defined by the individual adapter of the robotic system. Further aspects of this embodiment will become apparent from and elucidated with further embodiments described hereinafter.

In an exemplary embodiment, n equals 2. In this example a ball joint, as described herein, is used. In this example, one can tilt the marker device/marker array in two dimensions but one can also rotate it around the central axis that sticks out of the ball joint.

In an exemplary embodiment, n equals 2 and the medical instrument base can be rotated e.g. around its center axis and in addition can be rotated around another axis which is preferably perpendicular to the center of axis. In this case, the calculation can be constraint to two different rotations. In another exemplary embodiment, the degrees of freedom n equals 3 and the medical instrument base may be rotatable around two different rotational axes and in addition can be translated along a translational axis, which differs from or is equal to said two rotational axes.

According to another exemplary embodiment of the present invention, the movable attachment of the medical instrument base at the robotic system is configured for only allowing a fixation of the medical instrument base at the robotic system at two or more discrete positions.

This embodiment describes the advantageous fixation of the medical instrument base at the robotic system such that it can only be fixed in predefined orientations. This provides the technical advantage that the calculated value, i.e. the orientation determined by the method of the present invention, can be rounded to the next one known to be possible, as is defined in the next embodiment in more detail. This allows to come up with a very accurate result of the orientation determination.

According to another exemplary embodiment, the method comprises the step of comparing a result of the determination of the orientation of the medical instrument base with previously stored possible results based on said discrete positions. Furthermore, the method comprises the step of rounding the determined result to one of the stored possible results, which is closest to said result of the determination.

As the calculation will inherently have a finite accuracy, especially if at least one of the two measurement systems for measuring the movement data is not very accurate or there is uncorrected unequal latency of the two measurements of the two movements, it can be advantageous if the instrument can only be attached in defined orientations, for example every 10 or 20 degrees. This holds true because one can then round the calculated value to the next one known to be possible and thereby allowing a high precision orientation determination. Such possible and known results may be stored previously in any kind of storage unit like a look-up table or data storage unit comprised in the robot control system or external of the system. For example, in the embodiment shown in FIG. 2, the receiving section 203 of the robotic system, which receives the marker device 204 attached to the medical instrument base, may allow to fix the marker only in discrete rotational positions, for example by providing discrete engagement slots in the receiving section within the cylindrical housing of the receiving section 203. Also other mechanical solutions for constraining the fixation of the medical instrument base with the marker device at the robotic system to several distinct positions/orientations can of course be used.

According to another exemplary embodiment of the present invention, the medical instrument base is embodied as either a guiding tube configured for receiving a surgical instrument or as an instrument shaft of a surgical instrument.

In general, the medical instrument base facilitates the provision of the surgical instrument to be used by the medical practitioner. Either a guiding tube may be provided, which for example provides a center hole into which the medical instrument can be inserted and fixed. In another embodiment, the medical instrument base is provided as a shaft of the surgical instrument itself, as can be gathered from for example FIG. 3. The first alternative, i.e. the guiding tube, is shown in FIG. 2.

According to another exemplary embodiment of the present invention, the guiding tube is configured as a cylindrical tube, which is received by a cylindrical receiving section of the robotic system. The guiding tube is rotatable around a common cylindrical axis of the receiving section and the guiding tube. Furthermore, the guiding tube can be fixed relative to the receiving section at a plurality of discrete rotational positions only.

The receiving section may be in the TCP of the robotic system. It should be noted that the cylindrical axis is to be understood as a virtual rotational axis. Furthermore, this embodiment example allows for a very accurate orientation determination, since one can use the idea of rounding the calculated value to the next one known to be possible, as has been described hereinbefore in more detail. Further aspects of this embodiment will be described in the context of the embodiment of FIG. 2.

According to another exemplary embodiment of the present invention, the first movement data are acquired from at least one position sensor and/or from the motor control of the robotic system. Furthermore, the second movement data are acquired from an additional, preferably optical, tracking system for tracking movements of the medical instrument base by means of the marker device.

The position sensor or position sensors may be seen as the internal system of the robotic system which delivers accurate results regarding the position and/or orientation of the robotic arm and/or other components of the robotic system. Furthermore, the tracking system for tracking the medical instrument base may be an external system in the sense of being provided in addition to the robotic system. Therefore, it is made clear that in this embodiment of the present invention, the orientation of the marker device is determined in relation to the robotic system by comparing the information about a movement from both the at least one position sensor/motor control and from the external tracking system tracking the marker device.

According to another exemplary embodiment of the present invention, the medical instrument base is movably attached to the robotic system with a ball joint which can be freely rotated in three spatial dimensions.

In general, the medical instrument base is connected to the robotic arm via a joint. In this embodiment, however, the joint with the most degrees of freedom for the movement of the surgical instrument to be used with the medical instrument base is provided.

According to another exemplary embodiment of the present invention, the first movement data are measured in a first coordinate system and the second movement data are measured in a second coordinate system. The method further comprises the step of transferring the first and second movement data into the same coordinate system using an assumed relationship, preferably a default orientation, and comparing the determined orientation with the assumed relationship thereby deducing the actual orientation.

In this embodiment, the output of the method, i.e. the determined orientation, is the information that can be used in order to be able to transfer data from the first to the second coordinate system. In a further specified embodiment, the step of correcting the default orientation after the comparison has been carried out between the determined orientation and the assumed relationship.

According to another exemplary embodiment, the method comprises automatically detecting the start of an orientation determination process by a robot control system and initiating the steps of the first aspect (S1 to S4) based on the detected start.

According to another exemplary embodiment of the present invention, the method further comprises the steps of comparing the first movement data with a robotic minimum threshold regarding the amount of movement of the robotic system and quantifying the first movement data as significant if the comparison reveals that the first movement data are above the minimum threshold. Moreover, determining that the first and second movement data are consistent based on at least one predefined consistency criterion, is comprised as a method step. The method further comprises the step of determining that the first and second movement data are suitable for the orientation determination.

The method may thus comprise a check, whether the robotic system moved significantly or whether the detected movement should be ignored. This can be done purely automatically. Furthermore, the method comprises a consistency check and if they are not consistent the detected movements may be ignored and/or a warning signal may be generated for the user. Further, it must be noted that there are movements that do not provide the desired information, for example, if the instrument is moved along its center axis around which it can rotate, no information about the rotation around this axis can be determined. This embodiment automatically checks whether the acquired movement data qualify for the desired orientation determination described herein.

The following applications can make use of the present invention following the same principle:

It could be the case that the two movements are unrelated, e.g. if the medical instrument base is inserted into the mount of the robotic system, there will be strong movement indicating by the tracking system whereas the robotic system will indicate no movement. The magnitude of the movement can thus be used in an embodiment to check whether the two movements are correlated or not and thus qualify for the desired orientation determination or not.

Moreover, if a rotating movement is detected by the tracking system only whereas the robotic system indicates no movement, it is likely that the movement was performed in order to re-orient the marker device to the tracking system. In this case, the originally determined rotation stored in e.g. the robot control system can be adjusted by the extent of the rotation known from the tracking system. In an embodiment of the present invention, the method comprises such an adjustment.

Furthermore, if both the first and second movement data signal a movement but these readings are not related as they should be based on the geometrical constraints know to the system carrying out the method, then this can be seen as an indication that the arrangement of the marker device is not properly inserted into the mount of the robotic system and a corresponding warning can be put out to the user. In an exemplary embodiment of the present invention, such a corresponding warning signal is generated and part of the presented method.

Furthermore, in case there are multiple different instruments or medical instrument bases, e.g. carrying the same marker device in different angulations, the comparison of the movements can serve as means for automatic determination of the inserted instrument or the inserted medical instrument base. In an embodiment of the present invention, such an automatic instrument identification is comprised in the method.

Further, in case that multiple robotic systems are connected to a network of a navigation system, the movement of all possible robotic systems could be correlated to the tracking system thereby identifying which robotic system is currently used together with the navigation system. In an embodiment of the present invention, such a robotic system identification is comprised in the method described.

According to a second aspect of the present invention also relates to a program which, when running on a computer, causes the computer to perform one or more or all of the method steps described herein and/or to a program storage medium on which the program is stored (in particular in a non-transitory form) and/or to a computer comprising said program storage medium and/or to a (physical, for example electrical, for example technically generated) signal wave, for example a digital signal wave, carrying information which represents the program, for example the aforementioned program, which for example comprises code means which are adapted to perform any or all of the method steps described herein.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

According to another aspect of the present invention, a robot control system is provided, which is configured for carrying out the method of any of the embodiments and aspects described herein.

In preferred embodiments, the robot control system comprise one or more of the robotic system, the marker array, the medical instrument base, and the tracking system.

According to another exemplary embodiment of the present invention, the robot control system is configured for carrying out the following steps:
automatically detecting a start signal for carrying out the method according to any of aspects or embodiments mentioned herein, wherein the start signal is detected by the robot control system when:
a coarse manual positioning of the robotic system has occurred,
a movement of the robotic system and/or the medical instrument especially for the determination of the orientation is initiated,
a movement that is initiated for referencing position sensors or other necessary steps during the set-up of the robotic system has occurred, or
a movement has occurred that is initiated to drive to a desired target thereby guessing the orientation of the marker device e.g. by using a default orientation or the last known orientation.

In other words, the robot control system of the present invention in this embodiment is capable of detecting and/or differentiating such stimulated movements. Therefore, the step of automatically detecting a start signal may be seen as automatically generating a start signal when one or more of the mentioned movement stimulations are detected by the system carrying out the method, like e.g. the robot control system.

According to another exemplary embodiment of the present invention, a navigation system for computer-assisted surgery is presented wherein the system comprises a robot control system as described herein.

BRIEF DESCRIPTION OF THE DRAWINGS

In the following, the invention is described with reference to the appended figures which give background explanations and represent specific embodiments of the invention. The scope of the invention is however not limited to the specific features disclosed in the context of the figures, wherein FIG. 1 schematically shows a flow diagram of the method of the present invention.

DESCRIPTION OF EMBODIMENTS

Figure 1:
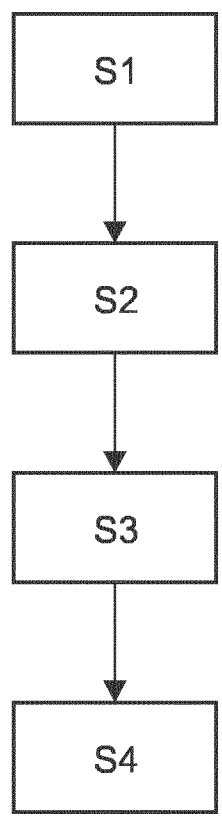

FIG. 1 illustrates the method steps of the method according to the first aspect which provides a computer-implemented medical method of automatically determining an orientation of a medical instrument base in relation to a robotic system. In other words, a method for automatic detection of instrument orientation for robotic surgery is presented.

In a first step S1, first movement data associated with a movement of the robotic system relative to a first reference are acquired. Preferably, such data acquisition can be carried out by one or more position sensors of the robotic system or by motor control of the robotic system. However, also other data acquisition means may be used.

Furthermore, in the step S2, the second movement associated with a movement of a marker device relative to a second reference are acquired. In a preferred embodiment, an optical tracking system is used which optically detects the marker device, as has been described hereinbefore in detail. In the embodiment shown in FIG. 1, the marker device is attached to the medical instrument base and the medical instrument base is movably attached to the robotic system. Therefore, also the marker is movable relative to the robotic system via a movement of the medical instrument base. This will become apparent from and elucidated with the further explanations following hereinafter. In a further step S3, the first and second movement data are compared and a comparison result is determined. This comparison result is used in step S4 for determining the orientation of the medical instrument base in relation to the robotic system.

Therefore, speaking generally about this aspect of the present invention, the orientation of the marker device in relation to the robotic system is determined by comparing the information about the movement detected by the tracking system as well as the movement detected by the robotic system. Therefore, in contrast to prior art approaches, in this aspect of the present invention, an additional tracking system is used, the marker device is movably attached to the robot and can be oriented individually, the medical instrument base can be mounted in several fixed orientations and the user does not have to select appropriate mounting orientations manually.

Figure 2:
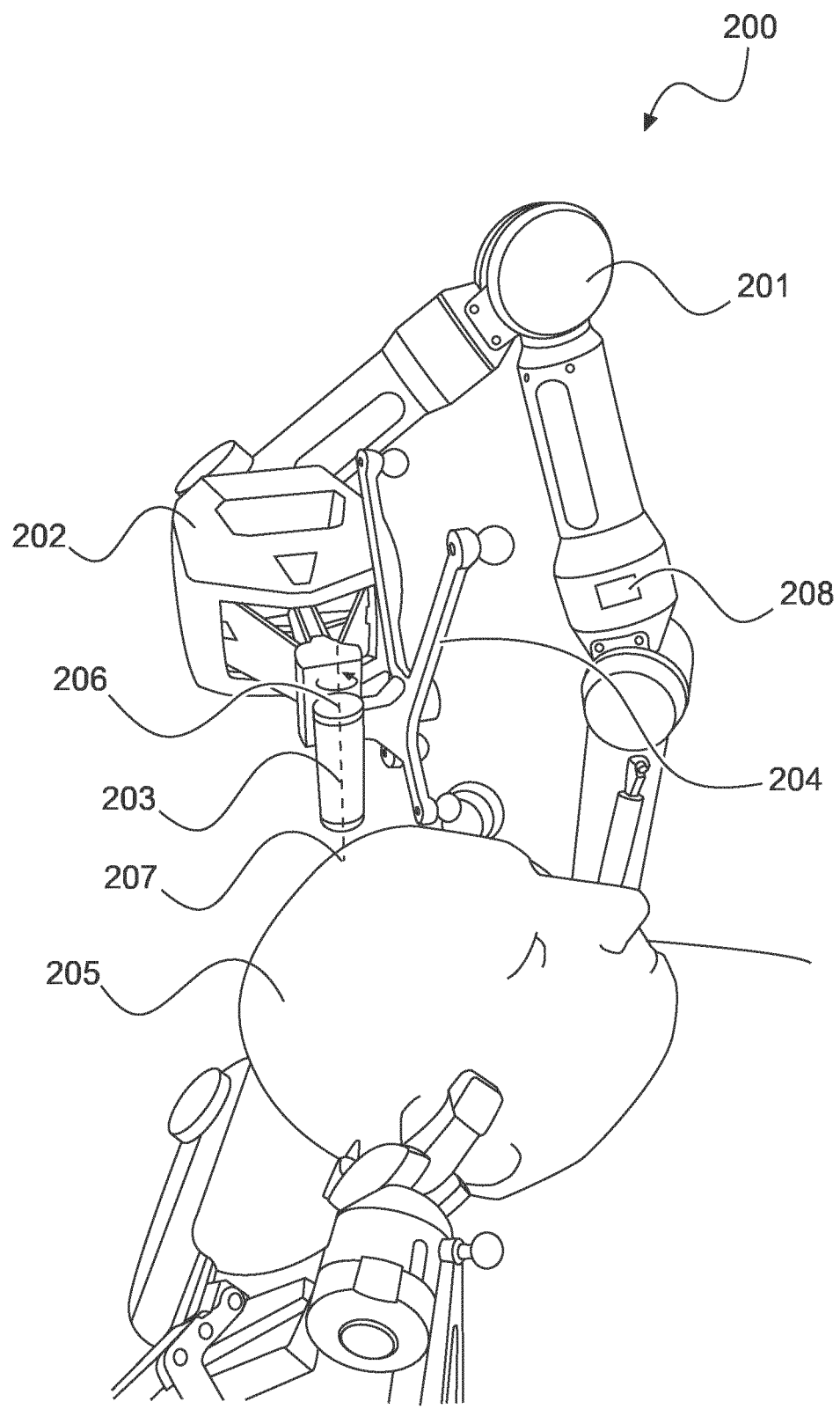
FIG. 2 schematically shows a robotic system with a robot control system using a guiding tube as a medical instrument base configured for receiving a surgical instrument according to an embodiment of the present invention.

FIG. 2 schematically shows a robotic system 200 which may use the method and the robot control system 208 according to an embodiment of the present invention. The robotic system 200 comprises robot arm 201 where at an end section 202, a receiving section 203 for receiving the medical instrument base 206 is comprised. The medical instrument base 206 in FIG. 2 is embodied as a guiding tube configured for receiving a surgical instrument. The medical instrument base 206 is movably attached to the robotic system 200. Furthermore, a marker device 204 is attached to the medical instrument base 206. The guiding tube 206 comprises a center hole into which a surgical instrument can be inserted in order to treat a patient which is schematically shown with sign 205 in FIG. 2. Based on the computer-implemented medical method of automatically determining an orientation of the medical instrument base 204 in relation to the robotic system 200 several technical effects can be achieved. An automatic detection of the orientation can be used for the subsequent calculation such as for example the automatic and efficient precise alignment to a target trajectory or can be used for a correct positioning assistance for a robot arm 201 of the robotic system 200.

In the embodiment of FIG. 2, the guiding tube is movable relative to the robotic system 200 only along the rotational axis which extends through the center borehole of the guiding tube. The virtual rotational axis 207 is indicated by a dashed line in FIG. 2. Therefore, the guiding tube 206 is movable relative to the robotic system 200 especially to the receiving section 203 of the robotic system 200 in one degree of freedom only. Therefore, the robot control system 208 used by the robotic system 200 can run the method as described with respect to FIG. 1, but can in addition set constraints for the step of determining the orientation of the guiding tube 206. Said constraints are associated with this degree of freedom describing the only allowed movement of the medical instrument base and indirectly thus of marker device 204, which is the rotational movement around rotational axis 207. Furthermore, the guiding tube 206 can be fixed with respect to the robotic system only at two or more discrete rotational positions. For example, ten rotational positions may be foreseen by means of corresponding notches or slits in the receiving section 203 into which the guiding tube 206 can be placed for fixation. This allows for comparing a result of the determination of the orientation, i.e. the result of the steps S1 to S4 shown in FIG. 1, of the guiding tube with previously stored possible results based on said discrete positions. This again allows rounding the determined result to one of the stored possible results which is closest to said result of the determination. This allows for the benefit of a very accurate determination result, may save computational effort and may accelerate carrying out the computer-implemented medical method.

In contrast to prior art solutions, the user of the robotic control system 208, which is configured for carrying out a method as described in FIG. 1, does not have to trust the position sensors of the robotic systems. Moreover, with the system and method explained for FIG. 2 the usability of the marker device 204 is not impaired by not having the flexibility to adequately orient it. Thus, line of sight issues such that the marker device 204 can no longer be detected or only detected with reduced accuracy are avoided by the system and method explained for FIG. 2. Moreover, in contrast to some prior art approaches, the system and method explained for FIG. 2 do not require additional manual steps. In general, the system and method explained for FIG. 2 may increase the precision of the robot assisted surgery.

Figure 3:
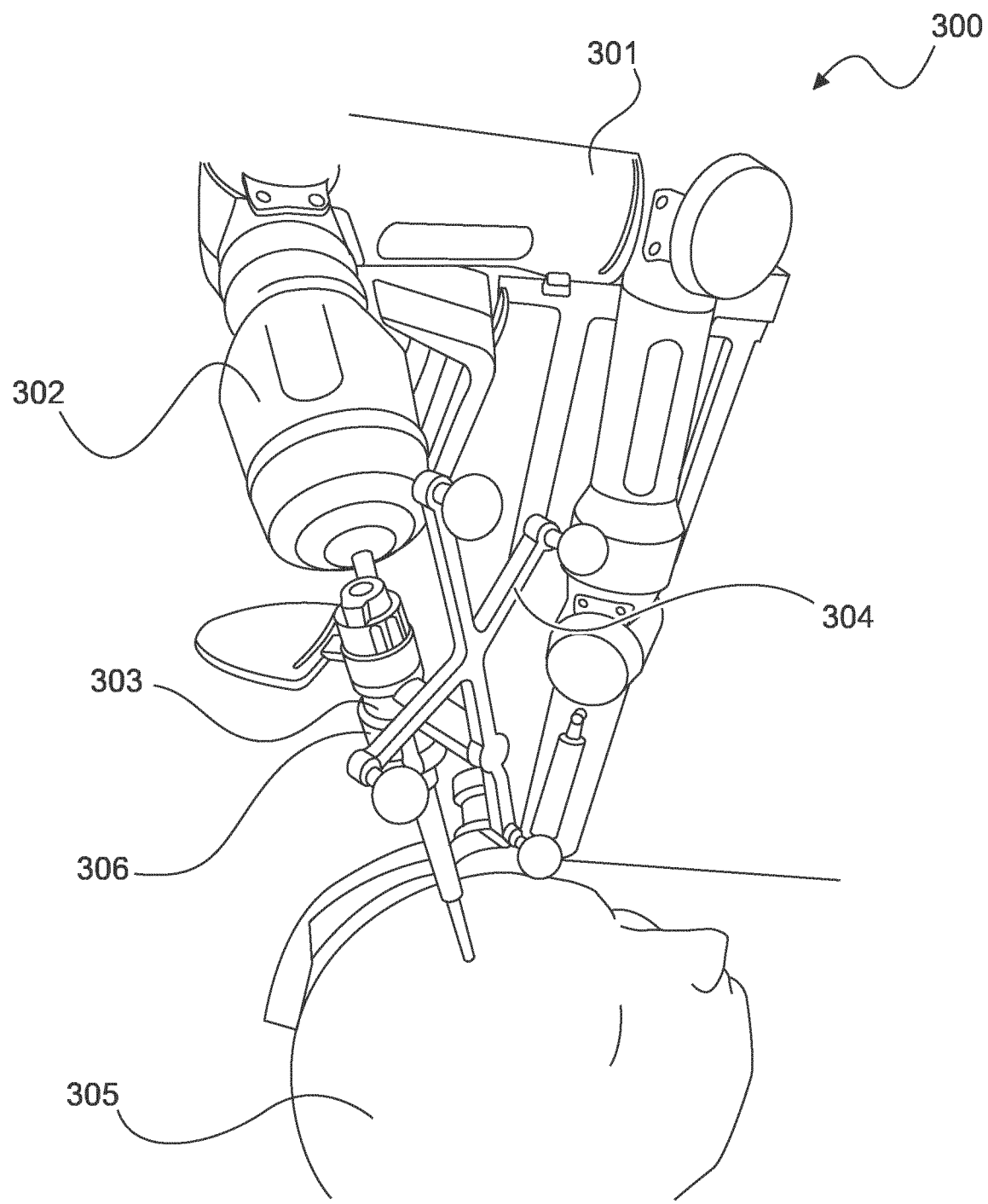
FIG. 3 schematically shows a robotic system with a robot control system using a shaft of a surgical instrument as medical instrument base according to an exemplary embodiment of the present invention.

FIG. 3 schematically shows a robotic surgery system 300 using a robot control system and the computer-implemented medical method according to an exemplary embodiment of the present invention. The system 300 comprises the robot arm 301 which in contrast to previous FIG. 4 comprises a different front section 302 to which the medical instrument base 303 is attached. In the embodiment of FIG. 3, the medical instrument base 303 is realized as an instrument shaft of a surgical instrument. A marker array 304 is attached to the shaft of the surgical instrument 303 and the shaft is rotatably attached to the robotic system 300. An exemplary patient head at which a surgical procedure can be carried out with the robotic system 300 is shown in FIG. 3 with reference sign 305. The computer-implemented method of automatically determining the orientation of the instrument shaft 303 in relation to the robotic system 300 may be carried out for example by a processor or a control unit comprised in the robotic system 300. However, in this and also in any other exemplary embodiments of the present invention, the computer-implemented medical method may also be carried out at a remote location using for example cloud computing, as was described in more detail hereinbefore. In particular, the robotic system 300 may be controlled by a navigation system for computer-assisted surgery which comprises a calculation unit that carries out the steps of said computer-implemented medical method.

The system 300 may acquire first movement data which are associated with a movement of the robotic system 300 relative to a first reference, for example the base of the robotic system 300. Preferably, position sensors or motor control of the robotic system 300 may be used to acquire said first movement data. Moreover, second movement data associated with a movement of the marker device 304 relative to a second reference are acquired. This may particularly be carried out when using an additional optical tracking system in which a second reference is used for said tracking. Since the marker device 304 is attached to the instrument shaft 303 and since the instrument shaft 303 is movably attached to the robotic system, also the marker device 304 is movable relative to the robotic system 300. The system carrying out the method, e.g. the calculation unit or control unit (not shown here) of the robotic system, is further configured to compare the first and second movement data and thereby determines a comparison result. In a further step, the comparison result is used for determining the orientation of the instrument shaft 303 in relation to the robotic system 300.

In a preferred embodiment, at least an initial and final position of the robotic system 300 are acquired and in the same way, an initial and final position of the marker device 304 are acquired. The calculation unit or control unit may then determine a relative movement of the robotic system 300 from its initial to its final position and in analogue way may determine a relative movement of the instrument shaft 303 from its initial to its final position. During carrying out the step S4, as described with respect to for example FIG. 1, the relative movement of the robotic system 300 is compared with the relative movement of the instrument shaft 303 and thereby the orientation of the instrument shaft 303 in relation to the robotic system is determined.

In a similar way to the embodiment described with respect to FIG. 2, the instrument shaft 303, to which the marker array 304 is attached, is rotatable along the center axis and can thus rotate around the cylindrical receiving section 306 of the robotic system 300 in which the shaft is received. However, also other degrees of motional freedom of the medical instrument base relative to the robotic system 300 can be realized, as has been explained hereinbefore in more detail. In a preferred embodiment of the robotic system 300 shown in FIG. 3, it can be taken into account that the determination of the orientation will inherently have a finite accuracy, especially if at least one of the two systems acquiring the first and second movement data are not very accurate or in case there is uncorrected unequal latency of said two measurements. It can thus be advantageous if the medical instrument base, here instrument shaft 303, can only be fixed to the end part of the robotic system by which the medical instrument base is received, in defined orientations. For example, the system 300 may only allow a fixation of the shaft 303 at the receiving section 306, every 10 or 20 degrees because one can then round the determined orientation value to the next one known to be possible and thereby come up with a very accurate result. Such possible and known results may be stored previously in any kind of storage unit like a look-up table or data storage unit comprised in the system 300 or external of the system 300. In this embodiment of robotic system 300, the movably attachment of the instrument shaft 303 at the robotic system 300 is configured for allowing a fixation of the shaft at the robotic system 300 at two or more discrete positions only. As an alternative to the cylindrical receiving section 306, a ball joint may be used which can be freely rotated in three spatial dimensions. However, in the embodiment shown in FIG. 3, as well as in the embodiment shown in FIG. 2, the medical instrument base 303 and 206, respectively, are movable relative to the respective robotic system in one degree of freedom only. Therefore, when carrying out the corresponding computer-implemented medical method of automatically determining the orientation of the medical instrument base 303 or 206 in relation to the respective robotic system 200 or 300, a constraint is set for the step of determining the orientation of the medical instrument base 303 since only the difference in rotation around this axis needs to be inspected. This may save computational effort and may accelerate carrying out the computer-implemented medical method.

Figure 4:
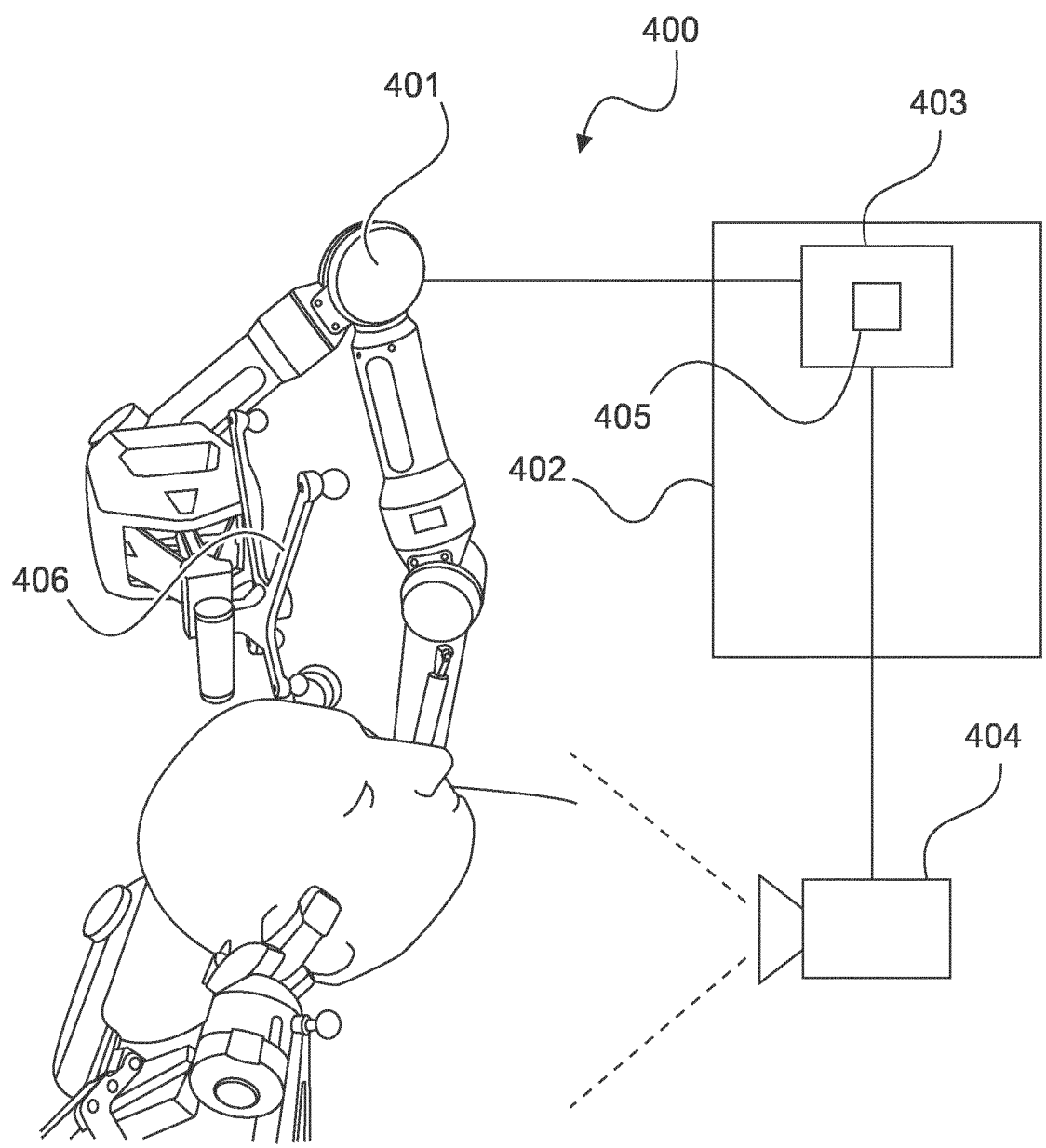
FIG. 4 schematically shows a navigation system for computer-assisted surgery according to an exemplary embodiment of the present invention.

According to another exemplary embodiment of the present invention, FIG. 4 shows a system 400 comprising the robot system 401 and the navigation system for computer-assisted surgery 402 which itself comprises a robot control system 403. In the robot control system 403, a calculation unit or a control unit 405 is comprised which is configured for carrying out the method as presented herein. The navigation system 402 is connected to the robotic system 401 and to the second, external tracking system 404, which can exemplarily be embodied as an optical tracking system. It is referred to this tracking system as external, since it is not comprised within the robotic system 401. In contrast to position sensors or motor control of the robotic system 401, which are used for gathering the first movement data of the method presented herein, tracking system 404 provides for the second movement data relating to the movement of the marker device 406.

Figure 5:
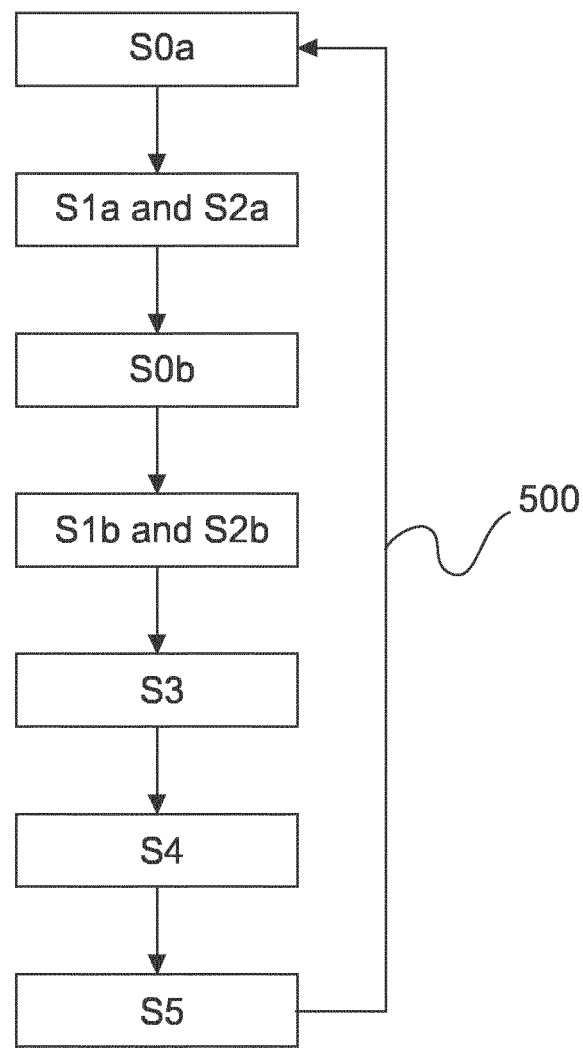
FIG. 5 schematically shows a flow diagram of an embodiment of the method of the present invention.

FIG. 5 schematically shows a flow diagram of another exemplary embodiment of the computer-implemented medical method of the present invention. In a first step S0a, the start of the orientation determination process is detected. This is done, for example, if the robotic system, the robot control system or the navigation system as described herein detects one of the following situations. A start signal may be generated indicating that the process of orientation determination has started.

For example, if a coarse manual positioning of the robotic system, e.g. in the surgical field, is detected, said start may be detected.

Moreover, the start of the orientation determination process as described herein by the computer-implemented medical method may be detected when a movement that is initiated explicitly to determine the orientation.

Alternatively, the start of the orientation determination process can be detected when the movement is initiated for referencing position sensors or other necessary steps during e.g. the setup of the robotic system.

Alternatively, the start of the orientation determination process can be detected when a movement is initiated to drive to a desired target thereby guessing the orientation of the marker device, e.g. by using a default orientation or the last known orientation.

Subsequently, the initial position of the robot arm or mechatronic arm of the robotic system and the marker device in relation to a respective reference is recorded, see steps S1a and S2a in FIG. 5. The system (i.e. the robotic system, the robot control system or the navigation system described herein) may further detect the end of the orientation determination process which is done in step S0b. After the detection of the end of the orientation determination process, the final position of the robot arm or mechatronic arm and the marker device in relation to the respective reference is recorded in steps S1b and S2b. In step S3, relative movements of the robot arm and the medical instrument base are calculated from the respective initial to the respective final position. In step S4, the relative movements which have been calculated in step S3 are compared thereby determining the orientation of the medical instrument base in relation to the robotic system. In step S5, the result of the orientation determination is rounded to the next possible discrete orientation, since the embodiment of FIG. 5 describes an embodiment where only a fixation of the medical instrument base at the robotic system at two or more discrete positions is allowed between which the medical instrument base can be moved. The rounded orientation result is used again in another iteration or a further use of this computer-implemented medical method of automatically determining the orientation as indicated by arrow 500.

Figure 6:
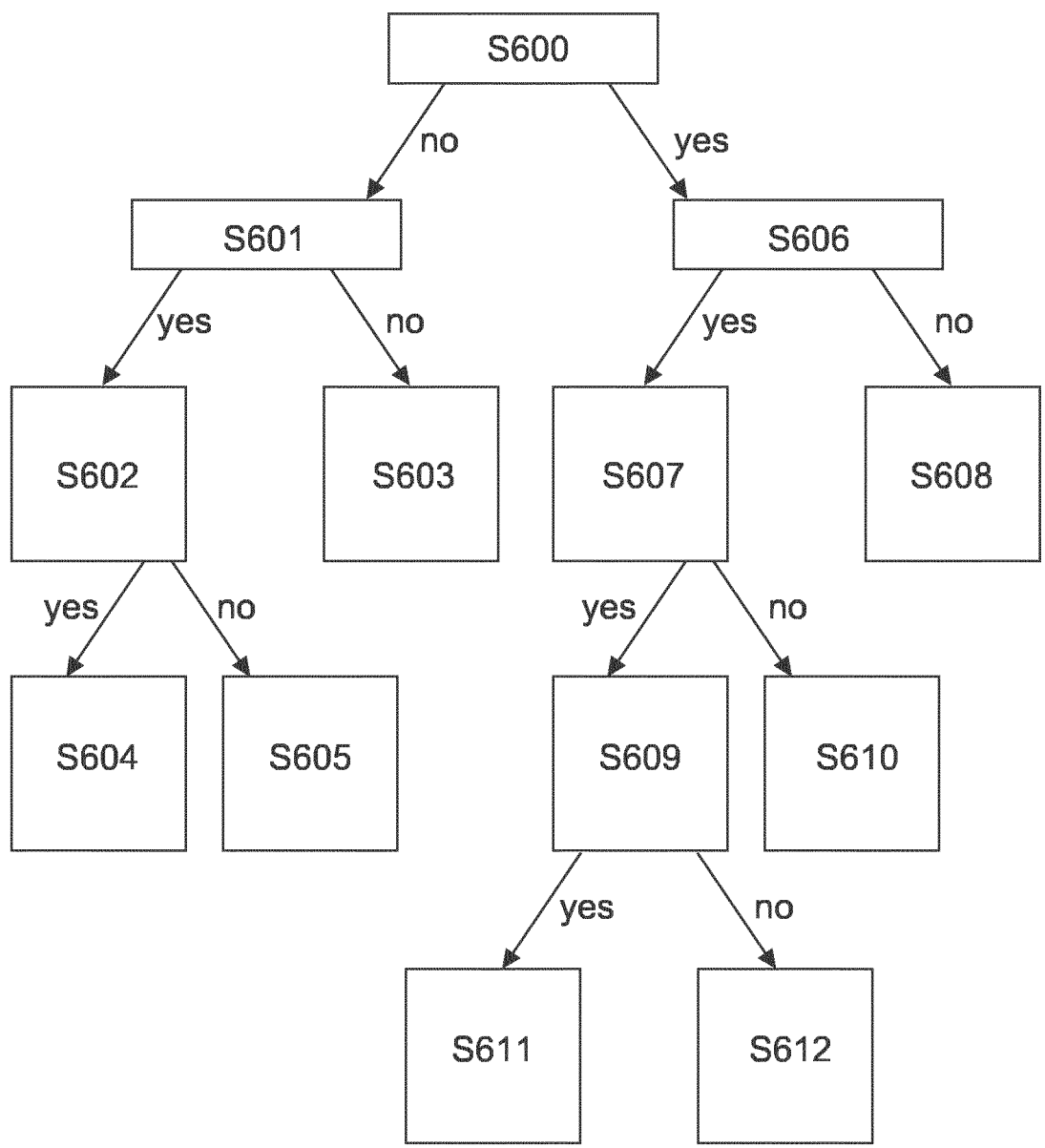
FIG. 6 schematically shows an example of a flow diagram in which the method of the present invention as described in FIG. 1 can be used.

FIG. 6 schematically shows a flow diagram of an example in which the present invention may be used. In particular, the computer-implemented medical method as has been described hereinbefore in for example FIG. 1 is carried out in the example of FIG. 6 in step 611. However, a robotic system, a robot control system or a navigation system for computer-assisted surgery (referred to hereinafter as the system) as described herein may in addition be configured for making several decisions as will be described now in more detail.

In step S600, such a system may decide whether the robotic system/mechatronic arm moved significantly. The system may thus be configured for comparing movement data of the robotic system or the mechatronic arm with for example a predefined significance threshold value. If the decision is "no", step S601 follows in which it will be decided by the system whether the marker device moved significantly. The system may thus be configured for comparing movement data of the marker device with a predefined threshold in order to decide whether the movement was significantly or not. If it is decided that the movement is significantly, step S602 follows whereas step S603 follows if the decision is "no". Step S603 defines that the system ignores said movement because the detected movement is insufficient. However, in step S602, the system is configured for determining whether the marker device movement is consistent with predefined geometric constraints of how the medical instrument base is attached to the robotic system. If the system decides that the marker device movement is consistent, i.e. if the answer is "yes", step S604 follows. In this case, a stored value of the orientation is adjusted using the detected movement of the marker device. However, if in the decision making of step S602 the answer is "no", step S605 follows defining that the movement is to be ignored because the marker device likely moved outside its mount.

In the following, the right branch of decision making shown in FIG. 6 is described in more detail. In particular, if after step S600, the decision whether the robotic system or the mechatronic arm moved significantly, the answer is yes, the system is configured for deciding whether the detected movements are consistent, which is done in S606. If the movements are considered to be consistent by the system, i.e. if the answer is "yes", step S607 follows. In step S607, the system is configured to determine whether the movement of the marker device is consistent with the way the marker device and the medical instrument base are mounted at the robotic system. If the movements are, however, considered not consistent in step S606, step S608 follows in which the system is configured to ignore said movements or is configured for issue a warning preferably to the user. Following step S607 it is determined by the system in step S609 whether the movement is suitable for determining the orientation of the medical instrument base relative to the robotic system. If the system considers it to be suitable, step S611 follows in which the steps S1 to S4 are carried out as described hereinbefore, for example with respect to FIG. 1. However, if in step S609 the movement is considered not to be suitable for an orientation determination, step S612 follows in which the system is configured to ignore the movement since the movement is unsuitable. Regarding step S609, it is clear for the skilled person, that there are movements that do not provide the desired information, for example if the instrument is moved along its center axis only, no information about the rotation around this axis can be determined, if one considers for example the embodiment examples of FIGS. 2 and 3. Further implementations are clear for the skilled person as they are in his working environment after being provided with the disclosure defined herein.

The invention claimed is:

1. A computer-implemented method of automatically determining an orientation of a medical instrument base in relation to a robotic system, the method comprising:
    acquiring time resolved first movement data associated with a movement of the robotic system relative to a first reference, wherein the acquiring the time resolved first movement data comprises defining a start time point associated with an initial position of the robotic system and an end time point associated with a final position of the robotic system, and recording at least the initial position of the robotic system and the final position of the robotic system; and
    acquiring time resolved second movement data associated with a movement of a marker device relative to a second reference, wherein the acquiring the time resolved second movement data comprises defining a start time point associated with an initial position of the marker device and an end time point associated with a final position of the marker device, and recording at least the initial position of the marker device and the final position of the marker device, wherein the start time points designate the same time point and the end time points designate the same time point,
    wherein the marker device is attached to the medical instrument base,
    wherein the medical instrument base is movably attached to the robotic system, the method further comprising:
        determining a relative movement of the robotic system from the start time point associated with its recorded initial position to the end time point associated with its recorded final position;
        determining a relative movement of the medical instrument base from the start time point associated with its recorded initial position to the end time point associated with its recorded final position;
        determining that the time resolved first movement data and the time resolved second movement data are suitable for determining the orientation;
        comparing the time resolved first movement data and the time resolved second movement data and determining a comparison result, wherein comparing the time resolved first movement data and the time resolved second movement data comprises comparing the relative movement of the robotic system with the relative movement of the medical instrument base from the start time point to the end time point; and
        determining, using the comparison result, the orientation of the medical instrument base in relation to the robotic system,
    wherein the acquisition of the time resolved first movement data is carried out marker-less.

2. The method according to claim 1,
    wherein the first movement data are acquired from an encoder of the robotic system as encoder data.

3. The method according to claim 2,
    wherein the encoder data are measured in a first coordinate system, and
    wherein the second movement data associated with the movement of the marker device are measured in a second coordinate system.

4. The method according to claim 1,
    wherein the robotic system is actuator-less.

5. The method according to claim 1,
    wherein the first reference is a base of the robotic system,
    wherein the marker device is embodied as a marker array used in combination with an optical tracking system, and
    wherein the second reference is either a second marker array or a reference of the optical tracking system.

6. The method according to claim 1, the method further comprising:
    using the determined orientation of the medical instrument base in relation to the robotic system for controlling the robotic system to align the medical instrument base to a target trajectory, or to provide positioning assistance for a mechatronic arm of the robotic system.

7. The method according to claim 1,
    wherein the medical instrument base is movable relative to the robotic system in n degrees of freedom, the method further comprising:
        setting constraints for determining the orientation of the medical instrument base, wherein said constraints are associated with said n degrees of freedom.

8. The method according to claim 1,
    wherein attachment of the medical instrument base at the robotic system is configured for allowing a fixation of the medical instrument base at the robotic system at two or more discrete positions only.

9. The method according to claim 8, the method further comprising:
    comparing a determined result of the determining the orientation of the medical instrument base with previously stored possible results based on said discrete positions; and
    rounding the determined result to one of the stored possible results which is closest to said determined result of the determining the orientation.

10. The method according to claim 1,
    wherein the medical instrument base is embodied as either a guiding tube configured for receiving a surgical instrument or as an instrument shaft of a surgical instrument.

11. The method according to claim 10,
wherein the guiding tube is configured as a cylindrical tube which is received by a cylindrical receiving section of the robotic system,
wherein the guiding tube is rotatable around a common cylindrical axis of the cylindrical receiving section and the guiding tube, and
wherein the guiding tube can be fixed relative to the cylindrical receiving section at a plurality of discrete rotational positions only.

12. The method according to claim 1,
wherein the first movement data are acquired from at least one position sensor and/or motor control of the robotic system, and
wherein the second movement data are acquired from an additional tracking system for tracking the medical instrument base by tracking the marker device.

13. The method according to claim 1,
wherein the medical instrument base is movably attached to the robotic system with a ball joint which can be freely rotated in three spatial dimensions.

14. The method according to claim 1,
wherein the first movement data are measured in a first coordinate system, and
wherein the second movement data are measured in a second coordinate system, the method further comprising:
transferring the first and second movement data into the same coordinate system using an assumed relationship and comparing the determined orientation with the assumed relationship to deduce an actual orientation.

15. The method according to claim 1, wherein the first and second movement data correspond to first and second movements that occur sequentially.

16. A non-transitory computer-readable data storage medium storing a computer program containing program instructions, that when executed on at least one processor of a computer or loaded onto the at least one processor of the computer, causes the computer to perform a method of automatically determining an orientation of a medical instrument base in relation to a robotic system comprising:
acquiring time resolved first movement data associated with a movement of the robotic system relative to a first reference, wherein the acquiring the time resolved first movement data comprises defining a start time point associated with an initial position of the robotic system and an end time point associated with a final position of the robotic system, and recording at least the initial position of the robotic system and the final position of the robotic system; and
acquiring time resolved second movement data associated with a movement of a marker device relative to a second reference, wherein the acquiring the time resolved second movement data comprises defining a start time point associated with an initial position of the marker device and an end time point associated with a final position of the marker device, and recording at least the initial position of the marker device and the final position of the marker device, wherein the start time points designate the same time point and the end time points designate the same time point,
wherein the marker device is attached to the medical instrument base,
wherein the medical instrument base is movably attached to the robotic system, the method further comprising:
determining a relative movement of the robotic system from the start time point associated with its recorded initial position to the end time point associated with its recorded final position;
determining a relative movement of the medical instrument base from the start time point associated with its recorded initial position to the end time point associated with its recorded final position;
determining that the time resolved first movement data and the time resolved second movement data are suitable for determining the orientation;
comparing the time resolved first movement data and the time resolved second movement data and determining a comparison result, wherein comparing the time resolved first movement data and the time resolved second movement data comprises comparing the relative movement of the robotic system with the relative movement of the medical instrument base from the start time point to the end time point; and
determining, using the comparison result, the orientation of the medical instrument base in relation to the robotic system,
wherein the acquisition of the time resolved first movement data is carried out marker-less.

17. A robot control system for automatically determining an orientation of a medical instrument base in relation to a robotic system, the robot control system comprising:
a control unit comprising a processor and a memory device, wherein the processor is operable to execute program logic stored in the memory device to perform a method comprising:
acquiring time resolved first movement data associated with a movement of the robotic system relative to a first reference, wherein the acquiring the time resolved first movement data comprises defining a start time point associated with an initial position of the robotic system and an end time point associated with a final position of the robotic system, and recording at least the initial position of the robotic system and the final position of the robotic system; and
acquiring time resolved second movement data associated with a movement of a marker device relative to a second reference, wherein the acquiring the time resolved second movement data comprises defining a start time point associated with an initial position of the marker device and an end time point associated with a final position of the marker device, and recording at least an initial position of the marker device and a final position of the marker device, wherein the start time points designate the same time point and the end time points designate the same time point,
wherein the marker device is attached to the medical instrument base,
wherein the medical instrument base is movably attached to the robotic system, the method further comprising:
determining a relative movement of the robotic system from the start time point associated with its recorded initial position to the end time point associated with its recorded final position;
determining a relative movement of the medical instrument base from the start time point associated with its recorded initial position to the end time point associated with its recorded final position;

determining that the time resolved first movement data and the time resolved second movement data are suitable for determining the orientation;

comparing the time resolved first movement data and the time resolved second movement data and determining a comparison result, wherein comparing the time resolved first movement data and the time resolved second movement data comprises comparing the relative movement of the robotic system with the relative movement of the medical instrument base from the start time point to the end time point; and determining, using the comparison result, the orientation of the medical instrument base in relation to the robotic system, wherein the acquisition of the time resolved first movement data is carried out marker-less.

18. The robot control system according to claim 17, wherein the control unit is configured to perform the method, the method further comprising:

automatically detecting a start signal, wherein the start signal is detected by the robot control system when:

a coarse manual positioning of the robotic system has occurred, a movement of the robotic system and/or the medical instrument base especially for determining the orientation is initiated, a movement that is initiated for referencing position sensors or other necessary steps during set-up of the robotic system has occurred, or a movement has occurred that is initiated to drive to a desired target thereby guessing the orientation of the marker device by using a default orientation or last known orientation.

19. The robot control system according to claim 17, wherein the first movement data are acquired from an encoder of the robotic system as encoder data.

20. The robot control system according to claim 17, wherein the control unit is configured to perform the method, the method further comprising:

using the determined orientation of the medical instrument base in relation to the robotic system for controlling the robotic system to align the medical instrument base to a target trajectory, or to provide positioning assistance for a mechatronic arm of the robotic system.

* * * * *